United States Patent [19]

Cornwell

[11] Patent Number: 4,547,662
[45] Date of Patent: Oct. 15, 1985

[54] NONINTERFERENCE OPTICAL ERROR SENSING SYSTEM

[75] Inventor: Dean F. Cornwell, Palm Beach Gardens, Fla.

[73] Assignee: United Technologies Corporation, Hartford, Conn.

[21] Appl. No.: 475,801

[22] Filed: Mar. 16, 1983

[51] Int. Cl.[4] .............................................. G01J 1/20
[52] U.S. Cl. ..................................... 250/201; 250/216
[58] Field of Search ..................... 250/201, 203, 216; 330/4.3; 356/359; 350/290

[56] References Cited

U.S. PATENT DOCUMENTS

| 3,804,521 | 4/1974 | Sprague | 356/359 |
| 3,825,845 | 7/1974 | Angelbeck et al. | 330/4.3 |
| 4,129,775 | 12/1978 | O'Meara | 250/203 |
| 4,210,400 | 7/1980 | Misek | 356/359 |
| 4,243,877 | 1/1981 | Cruz | 250/201 |
| 4,295,741 | 10/1981 | Palma et al. | 250/201 |
| 4,405,232 | 9/1983 | Mansell | 250/201 |

Primary Examiner—David C. Nelms
Assistant Examiner—James Gatto
Attorney, Agent, or Firm—Eric W. Petraske

[57] ABSTRACT

A device for examining optical surfaces in an optical train for a laser employs radiation diffusely scattered from the surfaces as input to a noninterfering sampling system that can examine any optical surface in the total system from a single sampling position.

6 Claims, 3 Drawing Figures

U.S. Patent  Oct. 15, 1985  Sheet 1 of 2  4,547,662

NONINTERFERENCE OPTICAL ERROR SENSING SYSTEM

TECHNICAL FIELD

The field of the invention is sensing errors in an optical system, such as a chemical laser and its associated optical train.

BACKGROUND ART

Conventional means of testing for alignment errors or errors caused by thermal distortion or turbulence within a laser or the optical train associated with it is the use of a diffraction grating etched on a mirror surface or a dichroic beam splitter. Either of these sampling devices deflects a low power sample beam from the relatively high powered output beam and directs the sample beam onto a detection device such as a Hartmann Sensor. The Hartmann Sensor, which is conventional in the art, analyzes the sample beam to determine the tilt of the phase front, focus/de-focus and time dependent errors. Conventional analyzing means such as a programmed digital computer accept as input the signals from the Hartmann Sensor and control the mirrors—either controlling the tilt of a rigid mirror or controlling the surface configuration of a deformable mirror as is known in the art.

DISCLOSURE OF INVENTION

The invention relates to a system for sensing errors in an optical train which employs the diffusely scattered light from the surface of mirrors which scattered light is deflected by a sampling device that does not contact the main beam. The sampled radiation is deflected to a detection system which generates signals representative of misalignment of mirrors within the optical train.

An advantageous feature of the invention is that the sensor is able to detect errors in more than one mirror from the same sensor position.

A further advantageous feature of the invention is that a single detector may be used to sense deviations both up beam and down beam of the sampler position.

BEST MODE FOR CARRYING OUT THE INVENTION

Figure 1:
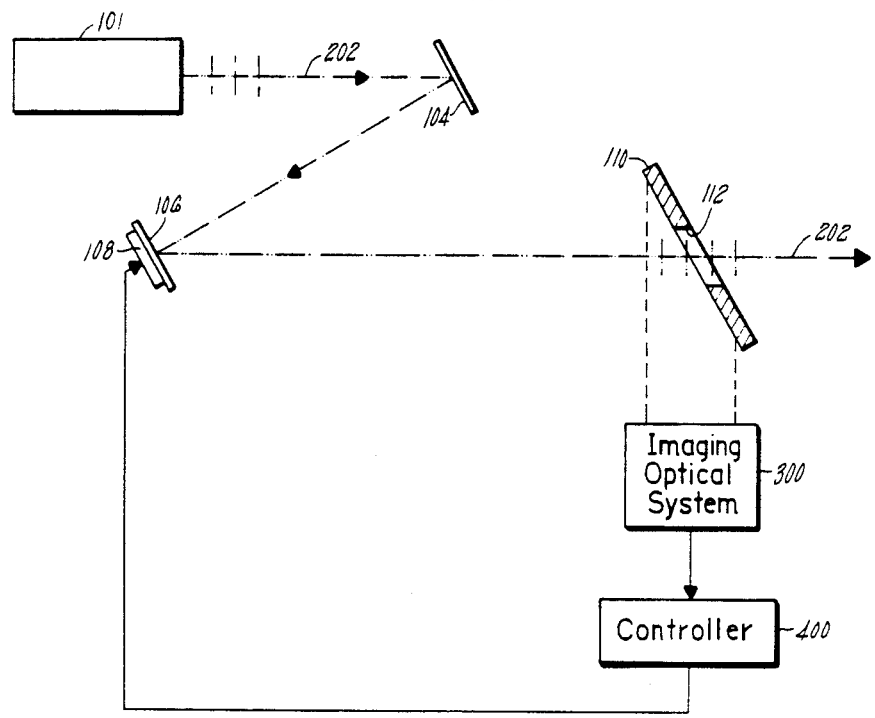
FIG. 1 illustrates schematically a simplified embodiment of the invention for controlling an optical system.

In FIG. 1, laser 101, illustratively a high power chemical laser, generates beam 202 which travels down beam from laser 101 and is deflected by flat turning mirror 104 and adaptive mirror 106, passing as an output beam through sampling device 110. Sampling device 110 is a flat mirror or a polished optical flat which has an aperture 112 through which beam 202 passes. Aperture 112 is sized to give a reasonable clearance for the passage of the beam so that only a very small amount of energy in the tail of the beam will strike deflector 110. This use of a sampler having an aperture is the characteristic distinction from prior art error sensing devices, which typically use a grating etched on a mirror surface to deflect a sample beam. In such prior art devices, of course, the grating will interfere with the main beam to a certain extent, possibly introducing additional distortion of its own, even as it generates a sample beam for error correction.

This invention takes advantage of the fact that any optical surface in a mirror, lens or window, no matter how perfect, will have a microstructure which diffusely scatters a small portion of the radiation incident on it. Well over 99% of the radiation is deflected in the main beam, of course. This diffusely scattered radiation travels in all directions, although the bulk of it travels close to the direction of the main beam. Sampler 110 deflects the diffusely scattered radiation which is close to, but not in, main beam 202 down to imaging optical system 300 which is described below. System 300 responds to the radiation and generates signals representing a focus error in one of the mirrors, a tilt in one of the mirrors or a non-azimuthal error in one of the mirrors. An advantageous feature of the invention is that the same optical system can respond to any mirror or optical surface upstream of sampler 110. These signals go to controller 400, which may be a programmed digital computer. Controller 400 responds to the error signals and generates control signals, in this case controlling deformable mirror 106 through piezoelectric actuators 108 on the back of it. The art of controlling a deformable mirror in response to error signals is well developed and is not part of this invention; which is concerned with detecting the errors in a noninterfering way.

Many different optical systems may be used to serve the function of system 300. Detector 300 must consist of an element or a series of elements that can form the image of at least one mirror in the optical train and generate signals relating to one or more of the image displacement, location of best focus, or aspect ratio of the image of some particular mirror in the optical train of the high power system. If only one mirror, such as mirror 106, is of interest, then a simple lens focusing the image of mirror 104 onto a detector such as a two-dimensional array of optical diodes would be sufficient. If it is desired to detect radiation scattered from more than one mirror, some way of detecting an image at different image planes corresponding to different mirrors would be required. Such a system is disclosed in U.S. Pat. No. 4,256,958 which is incorporated by reference.

The sampler device 110 and any optical elements within detector 300 will combine to form an equivalent simple lens having a focal length f. This equivalent lens will form a series of images of the two mirrors 106 and 104 at different distances from the equivalent lens according to the lens' maker's formula. If the distance from mirror 106 to the effective position of the equivalent lens is L106, then there will be an image of mirror 106 formed a distance L106' given by the lens' maker's formula. One or more of these images may be examined by the detecting device to derive information, as will be described below.

Assume that mirror 104 has been tilted by a small angle denoted by a. There will be no motion of beam 202 at the surface of mirror 104 and thus there will be no change in its image within optical detector 300. However, the beam is displaced at the surface of mirror 106 by an amount $d106 = 2a(L104 - L106)$ where L106 and L104 are the distances of the respective mirrors from the effective position of the equivalent lens and d106 is the displacement at the surface of mirror 106. It is straightforward to calculate the deviation of the image of the beam footprint at mirror 106 which is given by the equation $d106' = (L106'/L106)2a(L104 - L106)$. Thus, measurement of the deviation of the image of the footprint at mirror 106 gives a measurement of the angular error in mirror 104. It is straightforward to derive a similar equation for analyzing the motion of the image of mirror 104 to derive a measurement of the angular tilt of mirror 106. Even in the case where both mirrors are tilted, a matrix equation can be solved in order to derive the measurement.

$$\begin{bmatrix} a104 \\ a106 \end{bmatrix} = \frac{1}{(L104 - L106)} \begin{bmatrix} 0 & \frac{L106}{f} - 1 \\ \frac{L104}{f} - 1 & 0 \end{bmatrix} \begin{bmatrix} d104' \\ d106' \end{bmatrix}$$

Those skilled in the art will be easily able to extend this procedure to the case of more than two mirrors.

A similar technique can be used to provide a measurement of wavefront de-focus errors. Suppose that mirror 106 has a curvature caused by thermally induced substrate bending. It is desired to adjust mirror 106 to compensate for that, but first the amount of de-focus must be measured. If mirror 106 has a radius of curvature equal to R106, then the object distance of mirror 104 will be changed and will have a new object distance dL104, given by $$dL104 = L104 + 2\frac{(L104 - L106)^2}{R106}$$

The new location of the image of mirror 104 is $$dL104' = L104' + \frac{L104'}{L104} 2 \frac{(L104 - L106)^2}{R106}$$

A similar equation may be easily derived for the change in image d106' caused by distortion of mirror 104. Thus, if detector system 300 has means for detecting the distance at which the image of a mirror is sharpest, a conventional problem solved by a number of conventional means, then we have a means of sensing the de-focus error of the different mirrors.

A third test that can be made is to examine the image of the mirrors, the mirrors being assumed to be round, to see if the image is also round. An asymmetry in the image will imply an azimuthally non-symmetric aberration within the system.

Figure 3:
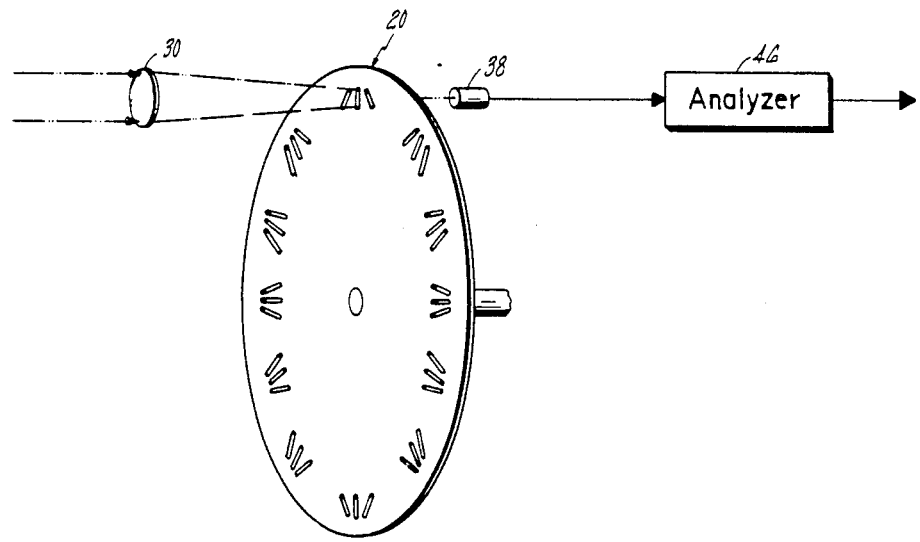
FIG. 3 illustrates an optical detector suitable for use in the invention.

The optical apparatus illustrated in U.S. Pat. No. 4,256,958 illustrates a detecting apparatus that may accomplish these different jobs. A simplified diagram of that invention is shown in FIG. 3 of this disclosure. Further details may be found in the patent itself. In FIG. 3, lens 30 is a supplementary lens which focuses incoming radiation from the sample beam onto detector 38, a conventional detector, and through wheel 20. Wheel 20 has a number of sets of three slits the size and orientation of which are disclosed in the referenced patent. Briefly, the edges of the slits in the radial direction of the disc may be used to detect transverse deviations in the mirror images; the position of the slits along the direction of travel of the sample radiation may be used to detect changes in the image plane and comparison of the signal shape within a group of three slits gives information on the symmetry of the image, thus permitting the measurement of all three aspects of the image that were described above. The limited number of sets of slits that may be imposed on a wheel poses a limitation on the amount of sampling that may be done with this system, of course. Those skilled in the art will easily be able to extend this detecting system to accommodate a reasonable number of measurements. The signals from detector 38 pass to analyzer 46 which stores selected signals in various groups depending on the longitudinal or transverse characteristic being measured and then passes selected stored signals on to controller 400.

Figure 2:
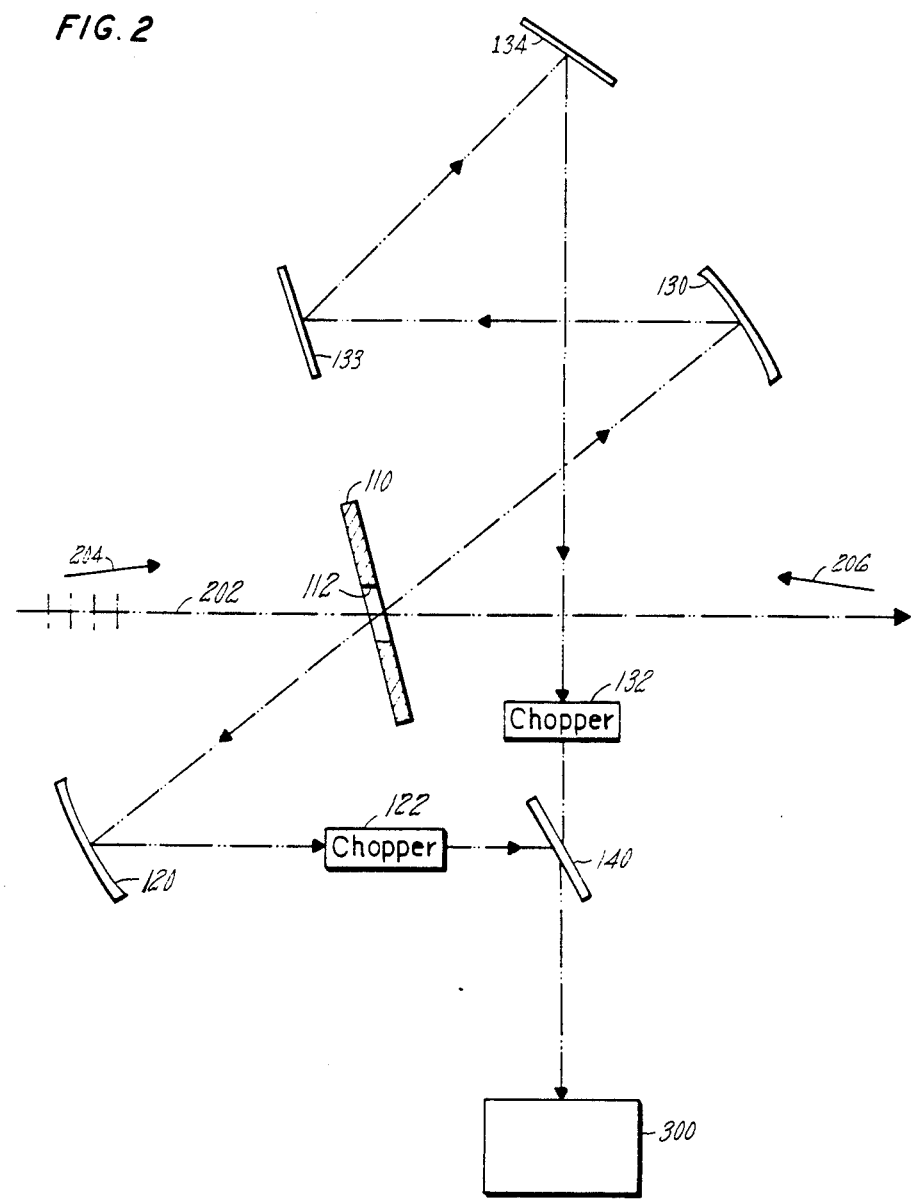
FIG. 2 illustrates an alternative embodiment of the invention which detects errors both up beam and down beam of a sampling place.

An improved apparatus according to the subject invention is disclosed in FIG. 2, in which beam 202 passes through sampler 110 as before, additional arrows 204 and 206 indicate generally the direction of propagation of radiation scattered at a small angle. Radiation scattered along direction 204, for example, strikes sampler 110, is deflected towards concave mirror 120 and thence to beam splitter 140, passing through chopper 122. Radiation scattered from elements down beam of sampler 110 travels generally along line 206, reflects at the back side of 110 and is deflected by concave mirror 130 and by flat turning mirrors 133 and 134 through chopper 132 and beam splitter 140 to detector 300. The function of choppers 122 and 132 is to facilitate separating up beam and down beam images, thus making the process of sorting out signals within detector 300 simpler. Conventional synchronism techniques for detecting radiation synchronous with one chopper or the other are well known to those skilled in the art and need no elaboration here. With a system such as that illustrated in FIG. 2, errors in any optical element in the whole system all throughout the optical train and even inside the laser itself may be detected. The image at the focal length of the equivalent lens described above, i.e. the image coming from infinity, will represent a combination of different elements within the optical resonator of laser 101. Individual optical surfaces within the laser will be imaged slightly away from the first focal point.

This system is especially useful for situations where it is desired to monitor different mirrors. One particular application is that of testing for signs of an imminent failure in a mirror surface, or the coating on the mirror surface. Typically, when the mirror surface is about to fail catastrophically, the scattered radiation goes up sharply. If controller 400 stores the average signal level from the different images and periodically compares them with some alarm value, the sharp rise in scattered radiation can be used as a trigger to shut down the laser before it is severely damaged by a failure of one of the mirrors.

The example illustrated has been concerned with mirror errors. Any other optical surface, such as a lens or window, will also be a source of diffusely scattered radiation and the same device may be used to monitor errors in the position of or the amount of radiation scattered from such optical surfaces.

I claim:
1. An apparatus for detecting errors in an optical system carrying a high power laser beam comprising:
   means for deflecting a portion of said laser beam to form an amount of sample radiation;
   means for collecting a test portion of said sample radiation;

means for focusing said test portion of said sample radiation to at least one image. each of which includes an amount of image radiation;

detector means for detecting image radiation in said at least one image and forming signals representative of said image radiation; and means for forming at least one set of image parameters from said representative signals; said image parameters being related in a predetermined manner to errors in said high power laser beam;

said means for deflecting a portion of said laser beam includes at least one single apertured optical surface intercepting said high power laser beam and being disposed within said optical system for deflecting said portion of said laser beam diffusely; and said means for collecting a test portion of sample radiation is a reflective element positioned outside said laser beam.

2. An apparatus according to claim 1, in which said detector means includes means for selecting preferentially a single image formed by said focusing means from a single optical surface within said optical system.

3. An apparatus according to claim 2, in which said detector means includes a radiation axis substantially along which said test portion of radiation is focused and includes means for forming signals representative of a position of sharpest focus of said at least one image along said axis.

4. An apparatus according to claim 2, in which said detector means includes a radiation axis substantially along which said test portion of radiation is focused and includes means for forming signals representative of transverse deviations of said at least one image from a predetermined reference position.

5. An apparatus according to claim 2, in which said detector means selects, sequentially, at least two single images formed by said focusing means.

6. An apparatus according to claim 1, in which said laser beam is carried from an up beam direction toward a down beam direction. in which said sample radiation is deflected both up beam and down beam and which said means for collecting a test portion includes an annular deflecting means having an annulus through which said laser beam passes and both up beam collecting means for collecting sample radiation deflected from said up beam direction toward said annular deflecting means and down beam collecting means for collecting sample radiation deflected from said down beam direction toward said annular deflecting means.

* * * * *